US009133074B2

(12) United States Patent
Jennings

(10) Patent No.: US 9,133,074 B2
(45) Date of Patent: Sep. 15, 2015

(54) PROCESS FOR THE CONVERSION OF CARBON DIOXIDE TO METHANOL

(71) Applicant: Air Fuel Synthesis Limited, Darlington (GB)

(72) Inventor: James Robert Jennings, Hutton Rudby (GB)

(73) Assignee: Avocet Fuel Solutions, Inc., Hockessin, DE (US)

( * ) Notice: Subject to any disclaimer, the term of this patent is extended or adjusted under 35 U.S.C. 154(b) by 0 days.

(21) Appl. No.: 14/360,424

(22) PCT Filed: Nov. 24, 2012

(86) PCT No.: PCT/EP2012/073547
§ 371 (c)(1),
(2) Date: May 23, 2014

(87) PCT Pub. No.: WO2013/076294
PCT Pub. Date: May 30, 2013

(65) Prior Publication Data
US 2014/0323600 A1 Oct. 30, 2014

(30) Foreign Application Priority Data
Nov. 25, 2011 (GB) .................................. 1120398.1

(51) Int. Cl.
*C07C 29/00* (2006.01)
*C07C 1/04* (2006.01)
*C07C 29/151* (2006.01)

(52) U.S. Cl.
CPC ............... *C07C 1/043* (2013.01); *C07C 29/151* (2013.01); *Y02E 50/18* (2013.01)

(58) Field of Classification Search
CPC ............................ C07C 33/02; C07C 1/0485
USPC .......................................... 518/702; 568/840
See application file for complete search history.

(56) References Cited

U.S. PATENT DOCUMENTS

| | | | |
|---|---|---|---|
| 1,569,775 A | | 1/1926 | Mittasch et al. |
| 2,692,274 A | | 10/1954 | Kölbel et al. |
| 4,282,187 A | | 8/1981 | Corbett et al. |
| 4,327,239 A | | 4/1982 | Dorrance |
| 5,602,289 A | * | 2/1997 | van Dijk ........................ 585/315 |
| 8,017,658 B2 | | 9/2011 | Tran et al. |
| 2005/0232833 A1 | | 10/2005 | Hardy et al. |
| 2006/0004111 A1 | | 1/2006 | Gagnon |
| 2006/0211777 A1 | | 9/2006 | Severinsky |
| 2008/0051478 A1 | | 2/2008 | Tran et al. |
| 2009/0320683 A1 | | 12/2009 | Hintz |
| 2010/0111783 A1 | | 5/2010 | Severinsky |
| 2010/0137457 A1 | | 6/2010 | Kaplan |
| 2014/0316016 A1 | | 10/2014 | Jennings |

FOREIGN PATENT DOCUMENTS

| | | |
|---|---|---|
| GB | 2 408 745 | 6/2005 |
| GB | 2 418 430 | 3/2006 |
| GB | 2 448 685 | 10/2008 |
| GB | 2 459 430 | 10/2009 |
| GB | 2 461 723 A | 1/2010 |
| WO | WO 93/16216 | 8/1993 |
| WO | WO 2006/036396 A2 | 4/2006 |
| WO | WO 2007/076257 A2 | 7/2007 |
| WO | WO 2008/033812 A2 | 3/2008 |
| WO | WO 2008/115933 A1 | 9/2008 |
| WO | WO 2009/048685 A1 | 4/2009 |
| WO | WO 2009/070273 A1 | 6/2009 |
| WO | WO 2009/108327 A1 | 9/2009 |
| WO | WO 2010/002469 A1 | 1/2010 |
| WO | WO 2010/112982 A1 | 10/2010 |
| WO | WO 2010/119254 A1 | 10/2010 |
| WO | WO 2013/076293 A2 | 5/2013 |
| WO | WO 2013/076293 A3 | 5/2013 |
| WO | WO 2013/076294 A1 | 5/2013 |

OTHER PUBLICATIONS

Xin et al, Chinese Journal of Chemical Engineering, 2009, 17(1), 88-94.*
An, X., et al., "Methanol Synthesis from $CO_2$ Hydrogenation with a Cu/Zn/Al/Zr Figrous Catalyst", *Chinese Journal of Chemical Engineering*, 17(10): 88-94 (2009).
Arakawa, H., et al., "Selective Conversion of $CO_2$ to Methanol by Catalytic Hydrogenation Over Promoted Copper Catalyst", *Energy Convers. Mgmt*, 33(5-8), 521-528 (1992).
Doss, B., et al., "Optimization of Methanol Synthesis from Carbon Dioxide and Hydrogen: Demonstration of a Pilot-Scale Carbon-Neutral Fuels Process", *Energy & Fuels*, 23: 4647-4650 (2009).
International Preliminary Report on Patentability/Written Opinion for International Application No. PCT/EP2012/073546, "Conversion of Carbon Dioxide to Hydrocarbons Via Hydrogenation"; Date of Mailing: May 27, 2014.
International Preliminary Report on Patentability/Written Opinion for International Application No. PCT/EP2012/073547, "Process for the Conversion of Carbon Dioxide to Methanol"; Date of Mailing: Jun. 5, 2014.
International Search Report for International Application No. PCT/EP2012/073546, "Conversion of Carbon Dioxide to Hydrocarbons Via Hydrogenation"; Date of Mailing: Sep. 9, 2013.
International Search Report for International Application No. PCT/EP2012/073547, "Process for the Conversion of Carbon Dioxide to Methanol"; Date of Mailing: May 7, 2013.
Lee, J.S., et al., "A Comparative Study of Methanol Synthesis from $CO_2/H_2$ and $CO/H_2$ over a $Cu/ZnO/Al_2O_3$ Catalyst", *Journal of Catalysis*, 144, 414-424 (1993).

(Continued)

*Primary Examiner* — Sudhakar Katakam
(74) *Attorney, Agent, or Firm* — Hamilton, Brook, Smith & Reynolds, P.C.

(57) ABSTRACT

Carbon monoxide conversion processes are described for the conversion of carbon monoxide via hydrogenation to methanol. The process utilizes initial carbon monoxide priming before introduction of 3:1 hydrogen/carbon dioxide mixture to the reactor. After the optimum reaction conditions are established the feed of carbon monoxide may be withdrawn and any required carbon monoxide provided via reactor effluent recycle. The process provides for enhanced catalyst performance and life.

23 Claims, 1 Drawing Sheet

(56) References Cited

OTHER PUBLICATIONS

Lee, S., et al., "Methanol Synthesis from Syngas", *Handbook of Alternative Fuel Technologies*, pp. 297-321 (2007).

Sun, J.T., et al., "Effect of Pre-Treatment on Methanol Synthesis from $CO_2/H_2$ Over $Cu/ZnO/Al_2O_3$," *Dept. of Chem. Engineering and Chem. Technology. Imperial College of Science. Technology and Medicine, London*, pp. 1128-1131 (1997).

*Non-Final Office Action for U.S. Appl. No. 14/360,420 "Conversion of Carbon Dioxide to Hydrocarbons Via Hydrogenation" dated: Sep. 3, 2014.

Hansen, J.B. and Hojlund Nielsen, P.E., "Methanol Synthesis", *Handbook of Heterogeneous Catalysis*, 2920-2949 (2008).

Chinchen, GC, et al., "The Activity of $Cu$—$Zno$—$Al_2O_3$ Methanol Synthesis Catalysts", preprints, *Am. Chem. Soc. Div. Fuel. Chem*, 29(5), 178 (1984).

Mitsui Chemicals Inc., "A New Leading Process for $CO_2$ to methanol", New Energy and Fuel, 2 pgs., Aug. 29, 2008.

* cited by examiner

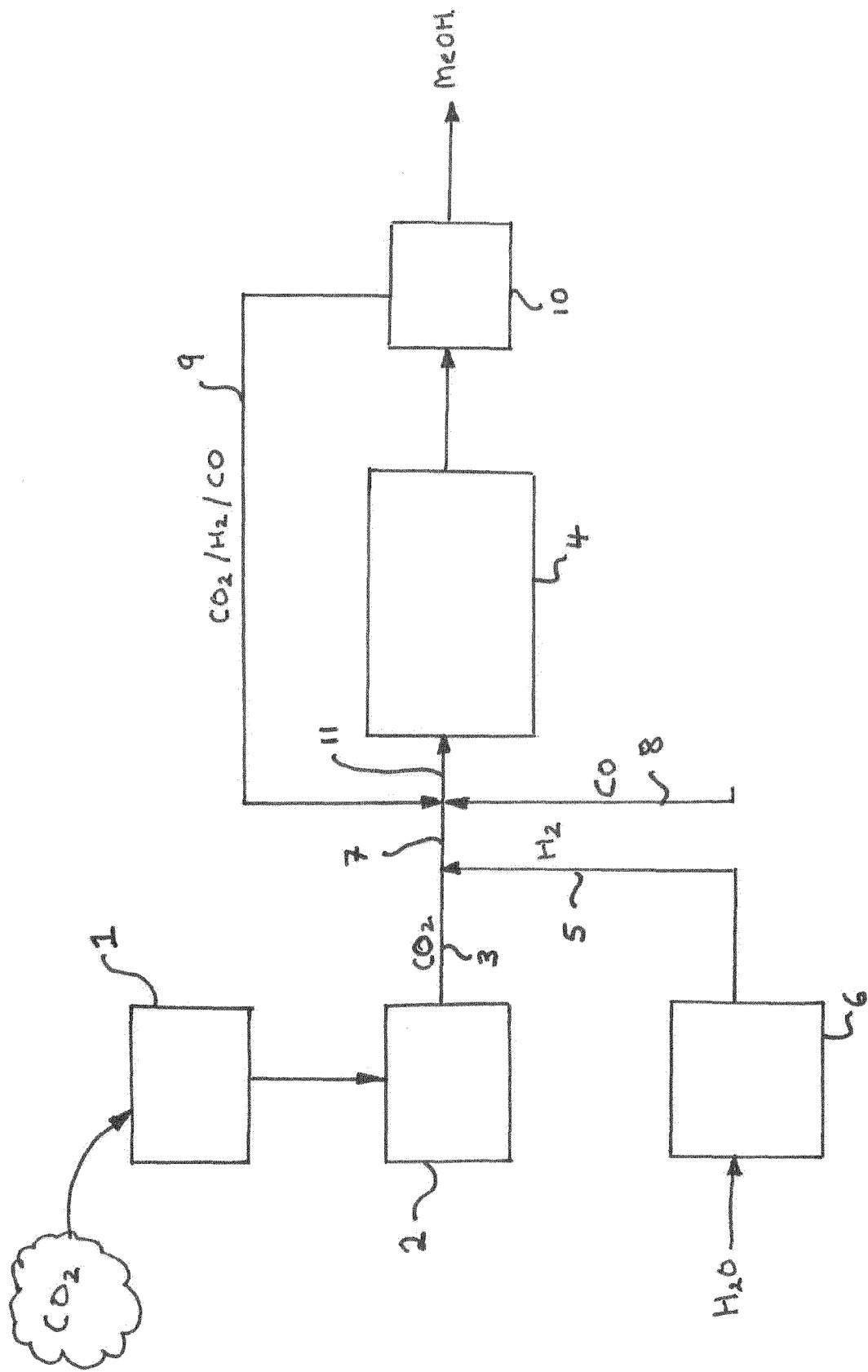

PROCESS FOR THE CONVERSION OF CARBON DIOXIDE TO METHANOL

This application is the U.S. National Stage of International Application No. PCT/EP2012/073547, filed Nov. 24, 2012, which designates the U.S., published in English, and claims priority under 35 U.S.C. §§119 or 365(c) to Great Britain Application No. 1120398.1, filed Nov. 25, 2011.

FIELD OF INVENTION

This invention relates to a process for the conversion of carbon dioxide into methanol via the hydrogenation of carbon dioxide.

BACKGROUND ART

The conventional industrial processes for the production of methanol have used a means to convert synthesis gas (a mixture of carbon monoxide, carbon dioxide, and hydrogen) into methanol. An early example of this approach is described in U.S. Pat. No. 1,569,775. This process used a mixed catalyst of chromium and manganese oxides. The process conditions were relatively extreme requiring high pressures ranging from 50 to 220 atm, and temperatures up to 450° C. The production of methanol from synthesis gas was further advanced in the early 1960s with the development of the more efficient ICI Low Pressure Methanol (LPM) process with the use of new catalysts (typically copper based) capable of operating at lower pressures and temperatures. The ICI LPM process is the most commonly used process for the production of methanol today. Today, the most widely used catalyst is a mixture of copper, zinc oxide with an alumina support, typically utilised as a fixed bed catalyst. The process is typically operated at 5-10 MPa (50-100 atm) and from 200 to 250° C.

Synthesis gas may be produced from coal, naphtha and natural gas sources. The common process is known as steam-methane reforming (SMR) and is carried out at moderate pressures of around 2-3 MPa (20-30 atm) and high temperatures (around 850° C.), over a nickel catalyst to produce syngas according to the chemical equation:

$$CH_4 + H_2O \rightarrow CO + 3H_2$$

This reaction is endothermic, and the heat transfer limitations place limits on the size of and the pressure in the catalytic reactors used. The reaction is carried out in the presence of an excess of steam, and is not selective due to the water gas shift reaction, during which, a significant proportion of the carbon monoxide formed is converted to carbon dioxide with the production of more hydrogen.

$$CO + H_2O \rightarrow CO_2 + H_2$$

Methane is also known to undergo partial oxidation with molecular oxygen to produce syngas, as the following equation shows:

$$2CH_4 + O_2 \rightarrow 2CO + 4H_2$$

This reaction is exothermic, and the heat given off can be used in-situ to drive the SMR reaction. When the two processes are combined, it is referred to as auto thermal reforming. This reaction is also not selective, and some of the methane and/or carbon monoxide is completely oxidized to carbon dioxide.

$$2CO + O_2 \rightarrow 2CO_2$$

$$CH_4 + 2O_2 \rightarrow CO_2 + 2H_2O$$

It is inevitable that synthesis gas will always contain a finite proportion of carbon dioxide, the precise amount being dependent upon the technology used for the manufacture of the synthesis gas, and the exact reaction conditions used.

The foregoing equations illustrate that the production of synthesis gas from methane via the steam reforming route produces three moles of hydrogen gas for every mole of carbon monoxide or four moles of hydrogen for every mole of carbon dioxide. The synthesis of methanol from syngas consumes only two moles of hydrogen gas per mole of carbon monoxide; this means that there is excess hydrogen using this approach. One method that could be utilised to deal with this excess hydrogen would be to inject carbon dioxide into the methanol synthesis reactor, where it will react with the excess hydrogen to form methanol according to the equation:

$$CO_2 + 3H_2 \rightarrow CH_3OH + H_2O$$

Alternatively, the hydrogen may be recovered and used elsewhere within the petrochemical complex.

The hydrogenation of carbon dioxide is said to be faster than that of carbon monoxide and according to academic literature carbon dioxide should be considered as the primary source of carbon in methanol synthesis (Lee, J. S, et. al. *J. Catal.* 1993, 144, 414-424). Other work has shown that the production of methanol from a synthesis gas that contains carbon dioxide, occurs mainly from the carbon dioxide component, at least in the initial stages of the reaction (Chinchen, G C et al, preprints, Am, Chem, Soc. Div, Fuel, Chem, 29(5), 178, (1984).

Due in part to global warming and climate change there is a growing interest in the methanol economy and alternative routes to methanol than the conventional ICI LPM process, which uses syngas. Growing attention is now being focused on the use of carbon dioxide from such sources as carbon capture and storage (CCS), carbon dioxide capture from flue gases or carbon dioxide waste from industrial processes such as brewing. These sources of carbon dioxide have been considered for use in combination with hydrogen obtained from water electrolysis using renewable sources of energy although in principle the hydrogen could be sourced from waste streams from conventional petrochemical processes or other sources.

One example of such a process for the conversion of carbon dioxide and hydrogen into methanol is described in Atkins, S. et. al. *Energy Fuels* 2009, 23, 4647-4650. In this reference, a process is described, which is based on the ICI LPM process in which conventional syngas is replaced as the feedstock by a mixture of carbon dioxide and hydrogen, which is then converted to methanol over a Cu/Zn catalyst in a fixed bed arrangement. The process was operated at relatively high pressures (1400-1800 psi) and temperatures (up to 260° C.). The maximum % conversion of carbon dioxide observed was less than 15 mole % and the reaction was very unselective when compared with normal methanol production. Both hydrocarbons and carbon monoxide were detected in the effluent from the main reactor.

Recent attempts to prepare methanol from carbon dioxide have suggested that the simple hydrogenation route is not facile and there are significant problems with the reactivity of carbon dioxide towards hydrogen in the synthesis of methanol (Mitsui Chemicals Inc.: "A New Leading Process for $CO_2$ to methanol". New Energy and Fuel, Aug. 29, 2008.

A further example is provided in published international application WO 2010/011504 A3. In this document a process is described in which all of the raw materials and energy for methanol production are obtained from a geothermal source.

These emerging processes for the utilisation of carbon dioxide/hydrogen feeds are not, as yet, optimized processes and have significant problems and challenges that are typically associated with such catalytic processes.

A major challenge in many catalytic processes is indentifying operating conditions, which ensure optimum utilization of the catalysts and/or process conditions and which operate with satisfactory selectivities. Catalysts have a useful life and must eventually be replaced or reconditioned in order to keep the process operating at the optimum conditions. Not all catalysts can be reconditioned, and copper/zinc catalysts in particular cannot be reconditioned and the poisoning and sintering of the catalysts is irreversible. The copper/zinc catalysts that are need for methanol synthesis fall into this category. The initial conditioning of the catalyst, the start-up conditions and ongoing operating conditions all have an impact on overall catalyst performance. Through any given cycle the catalyst activity will diminish and this is often compensated by changing the process to conditions that are even harsher on the catalysts resulting in accelerated catalyst deactivation. There is a typical tradeoff between the costs of catalyst replacement compared to the increased running costs to maintain activity.

This is a particular problem for catalysts used in processes for the conversion of carbon dioxide/hydrogen where harsh conditions may be required and catalyst life is shortened as a consequence.

DISCLOSURE OF THE INVENTION

The present invention is concerned with processes for the conversion of carbon dioxide to methanol, which utilize carbon monoxide in the early stages of the process to improve the initial or start-up operating conditions of the process and the subsequent life and activity of the catalysts used. In many of these processes (as described above for the conversion of carbon dioxide and hydrogen to methanol) the process conditions will result in a proportion of reverse water gas shift reaction, producing small quantities of carbon monoxide in the reactor effluent. The initial reactor conditions are set to keep the equilibrium carbon monoxide levels as low as possible as it is not desirable to produce large quantities of carbon monoxide as a waste product from the process.

With reference to the present invention it has been found that if a quantity of carbon monoxide is added to the carbon dioxide/hydrogen 1:3 mixture subsequent to activation of the catalyst by reduction in a hydrogen/nitrogen mixture, then this allows the subsequent process to be operated immediately under conditions closer to those pertaining to conventional methanol synthesis with a positive impact on operating conditions, selectivity and catalyst life. In the process of the present invention the reaction effluent is processed to recover methanol and to enable a mixture of hydrogen carbon dioxide and carbon monoxide to be recycled into the reaction, thus mimicking the normal process. Once the process has been initiated and recycle has commenced, the amount of introduced carbon monoxide may be reduced and eventually terminated, as the required carbon monoxide levels are generated within the reactor due to the reverse water gas shift. In essence the initial carbon dioxide hydrogen feed has carbon monoxide introduced to the feed to create a synthetic syngas mixture, which is subsequently maintained in the process due to carbon monoxide recycle as the initial carbon monoxide feed is removed. At this point the only feeds into the reactor are carbon dioxide (preferably from carbon dioxide capture from the atmosphere), hydrogen (preferably from the electrolysis of water using carbon neutral electricity) and reactor recycle. If the process needs to be shut down for any reason, it may be necessary to start up again with a temporary addition of carbon monoxide to the reactor feed.

Thus the present invention provides a process for the conversion of carbon dioxide to methanol via hydrogenation, which process comprises introduction of carbon monoxide to the carbon dioxide hydrogen feed to the reactor.

In a further embodiment the process comprises separation of non converted reactants from the reactor effluent for recycle to the reactor. In a preferred embodiment the non converted reactants comprises one or more of carbon dioxide, hydrogen and carbon monoxide. Thus any carbon monoxide formed in the reactor may be added, through recycle, to the incoming carbon dioxide/hydrogen feed enabling the introduction of non reactor carbon monoxide to the feed to be reduced or terminated. The recycle may be the combination of non-reacted carbon dioxide, carbon monoxide and hydrogen as mixture or they may be recycled as individual feeds to the corresponding feed to the reactor or they may be introduced to the reactor as binary mixtures with or without supplemental introduction of fresh feed of each component of the mixture.

In a further embodiment the effluent carbon monoxide is not separated from the carbon dioxide/hydrogen recycle. In one embodiment the recycle is combined with introduced hydrogen, carbon dioxide and/or carbon monoxide to provide the desired carbon monoxide level for optimum methanol production. In a preferred embodiment the process conditions are selected to provide the required level of carbon monoxide in the recycle to achieve carbon monoxide equilibrium without the need for continued introduction of carbon monoxide to the reactor.

It is preferred that the carbon dioxide is provided from recovery of carbon dioxide from the atmosphere, the oceans and/or the effluent streams of industrial or fermentation processes. There are various processes through which this may be achieved including adsorption such as amine based adsorption, high pressure absorption processes, membrane processes and cryogenic processes.

One preferred process for carbon dioxide capture and release is a two stage process where carbon dioxide is scrubbed from the air or stream comprising carbon dioxide with a scrubber preferably using sodium hydroxide. Examples of technology that may be used in this stage of the process are described in WO2010119254A1, WO2009070273A1, WO2006036396A2 and US2009320683A1. Other suitable processes for carbon dioxide recovery include high temperature carbonate/bicarbonate processes.

This first stage produces a sodium carbonate/sodium hydroxide mixture, which may be fed into an electrolysis cell where the feed is electrolysed to produce carbon dioxide, which may be fed to the reactor or intermediate storage. In a preferred embodiment the electricity for the electrolysis and the scrubbing stages is sourced from renewable source of electricity and most preferably carbon neutral sources of electricity. A suitable electrolysis process for the release of carbon dioxide from such mixtures is as described in published international patent application WO9316216A1, the whole contents of which are hereby incorporated by reference.

It is preferred that the hydrogen is provided from the electrolysis of water, preferably utilizing carbon neutral or renewable sources of electricity. One such source could be nuclear power.

Any water generated in the process may be recycled for electrolysis to hydrogen for use in the process.

It is preferred that the hydrogenation reaction is undertaken at 400° C. or less, preferably 350° C. or less and most preferably 300° C. or less. A preferred reaction temperature is between 150 and 300° C., most preferably 200 and 300° C., and most preferably 220 to 280° C.

It is preferred that the hydrogenation reaction is undertaken at a pressure of 20 MPa (200 atm) or less, preferably 15 MPa (150 atm) or less, and most preferably 10 MPa (100 atm) or less. It is preferred that the pressure is within the range of 5 to 20, more preferably 5 to 15 and most preferably 5 to MPa (50 to 100 atm).

The hydrogen and carbon dioxide may be introduced to the reactor in a 3:1 molar ratio. Any deviation from the 3:1 molar ratio will lead to an accumulation of the component in excess of the 3:1 stoichiometry, leading to a finite concentration of inerts passing through the reactor. It will become necessary to deal with this situation to maintain a satisfactory rate of production. This could entail monitoring the composition of the reactor effluent stream, and adjusting the hydrogen or carbon dioxide rates of flow, or alternatively, taking a small purge stream from the reactor and treating this separately, to maintain the composition of the recycle stream within an acceptable range.

The carbon monoxide may be introduced to the reactor feed of carbon dioxide and hydrogen at a level providing which allows the catalyst to function at an acceptable rate at an acceptable temperature.

In the process of the present invention the catalyst may be any suitable catalyst for the hydrogenation of carbon monoxide to methanol. Suitable catalysts are as described in Hansen, J. B. and Højlund Nielsen, P. E. 2008. Methanol Synthesis. Handbook of Heterogeneous Catalysis. 2920-2949. In a preferred embodiment the catalyst comprises Cu and ZnO on alumina. Preferably the content of copper oxide is 10 to 75% by weight, preferably 18 to 68% by weight, more preferably 30 to 62% by weight. The content of zinc oxide is 3 to 40% by weight, preferably 10 to 35% by weight, more preferably 20 to 30% by weight. A ratio of copper oxide to zinc oxide in the catalyst composition is not strictly limited and can be changed depending on conditions for a methanol synthesis reaction using said catalyst composition. It is preferable that copper oxide and zinc oxide are present in such proportions that a Cu/Zn atomic ratio is 0.5/1 to 20.0/1, preferably 0.8/1 to 15.0/1, more preferably 0.8/1 to 5/1. The catalyst may have performance enhancing additives present such as for example magnesia and manganese oxide etc. The catalyst composition is subjected to an activation treatment such as reduction with diluted hydrogen as is usually practiced, before being used in the process of the present invention. The diluents typically comprise nitrogen gas and methane.

In a preferred embodiment, the process of the present invention is integrated into downstream processes for utilization of the methanol produced by the process. One preferred integrated process is the methanol to gasoline process (MTG).

A present invention is exemplified and will be better understood upon reference to the following detailed description and examples when read in conjunction with the accompanying drawing and in which:

FIG. 1 is a schematic view of a preferred process according to the present invention.

BRIEF DESCRIPTION OF THE DRAWINGS

With reference to FIG. 1, there is exemplified a process for the conversion of carbon dioxide to methanol via hydrogenation. The carbon dioxide is captured from the atmosphere via the scrubber unit (1), which produces a sodium carbonate/sodium hydroxide mixture, which passes to an electrolyser unit (2), which utilises renewable and preferably carbon neutral electricity to electrolyse the sodium carbonate/sodium hydroxide mixture to produce carbon dioxide for the feed (3) for the reactor (4). The hydrogen required for the process and supplied through feed (5), which is combined with the carbon dioxide feed (3), is produced by the electrolysis of water in electrolysis unit (6), which utilises renewable and preferably carbon neutral electricity for the electrolysis. The carbon dioxide/hydrogen mixed feed (7) is passed into the reactor (4) for conversion to methanol. At start-up of the process a carbon monoxide feed (8) is combined with the carbon dioxide/hydrogen mixed feed (7) to produce a carbon dioxide/hydrogen/carbon monoxide feed (11) into the reactor (4). Once the reaction has been initiated and the reactor (4) has attained or is approaching steady state operation the carbon monoxide feed (8) is replaced with carbon monoxide obtained through carbon monoxide recycle (9) via separation from the methanol from the reactor via separation unit (10), and the carbon monoxide feed (8) is terminated and the mixed feed at (11) is now a carbon dioxide/hydrogen mixture.

EXAMPLE 1

Equipment

The test equipment consisted of a heated, one liter, fixed bed adiabatic reactor filled with a conventional $Cu/ZnO/Al_2O_3$ methanol synthesis catalyst. The reactor had means for introducing and controlling a feed gas to the reactor and means for automatically injecting reactant gases, carbon dioxide, hydrogen and carbon monoxide into the feed stream.

The unit was fitted with means for on-line analysis of the reactor effluent using gas chromatography (Shimadzu GC 2014) fitted with a twin detector system (Flame Ionisation and Thermal conductivity detectors) so that all the reaction components and products present in the reactor effluent could be detected and analysed. The equipment further consisted of means for the cooling and condensation of the reactor effluent; this enabled the products of the reaction to be condensed by cooling the gaseous effluent by indirect cooling so that the liquid products could be condensed and collected. The equipment had means for recycling unreacted non-product gases; these gases, after condensation, were then recirculated at pressure with added make-up gas to compensate for earlier conversion of feed gases to the desired product methanol. The point of recycle is immediately before the compressor which in turn is immediately before the heater and reactor. Make up gas is also injected immediately before the compressor.

Operating Conditions

The system was purged with nitrogen to remove air/oxygen in order to eliminate any explosion risk. The synthesis loop was then pressurised with carbon monoxide to a pressure of about 8 bar, by introduction of carbon monoxide to the reactor feed. No further carbon monoxide is added to the unit. The reactants carbon dioxide and hydrogen were then added in an appropriate ratio consistent with methanol synthesis to a pressure of about 70 bar, to the reactor feed. These reactants in the presence of introduced carbon monoxide were circulated through the reactor via the recycle loop. This circulating gas mixture was heated to a temperature in the range 185 to 210° C., without any further introduction of carbon monoxide.

As the temperature of the reactor reached 200° C. analysis of the reactor effluent indicated methanol formation as seen by the traces from the gas chromatograph. As methanol synthesis was established and had stabilised, the feed of carbon dioxide and hydrogen was adjusted as the previously added carbon monoxide was consumed so that at steady state, carbon dioxide and hydrogen were added at a molar ratio of 1:3.

As the carbon monoxide concentration in the recycle loop diminished to a low steady state value, the production of methanol was seen to be stable and unaffected by the reduction in carbon monoxide levels.

Previous reports in the literature have suggested that methanol synthesis is much more difficult when using a feed gas the only comprises carbon dioxide and is free from carbon monoxide. We do not see any reduction in catalyst performance when the reaction is initiated in the presence of carbon monoxide, even when no further carbon monoxide other than recycle is added after reaction has commenced.

The invention claimed is:

1. A process for the conversion of carbon dioxide to methanol via hydrogenation, which process comprises:
 a) introducing non-recycle carbon monoxide into an initial reactor feed of carbon dioxide and hydrogen for a period of time sufficient to initiate the hydrogenation reaction in a reactor comprising an activated catalyst, to produce reactor effluent comprising non-converted reactants and methanol;
 b) processing the reactor effluent to separate non-converted reactants from the methanol;
 c) recycling the non-converted reactants back into the reactor;
 d) terminating the introduction of non-recycle carbon monoxide to the reactor feed of carbon dioxide and hydrogen once recycling of the non-converted reactants has commenced according to step (c); and
 e) continuing to perform steps (b) and (c) during the hydrogentation process to produce methanol.

2. A process as claimed in claim 1, wherein the non-converted reactants comprises one or more of carbon dioxide, hydrogen and carbon monoxide.

3. A process as claimed in claim 1, wherein the recycle comprises a combination of non-reacted carbon dioxide, carbon monoxide and hydrogen as a mixture.

4. A process as claimed in claim 1, wherein the recycled reactants are recycled as individual feeds to the corresponding feed to the reactor.

5. A process as claimed in claim 1, wherein the recycled reactants are recycled as binary mixtures with or without supplemental introduction of fresh feed of each component of the mixture.

6. A process as claimed claim 1, wherein the carbon monoxide is introduced at the level for optimum methanol production.

7. A process as claimed in claim 1, wherein the process conditions are selected to provide the required level of carbon monoxide in the recycle to achieve carbon monoxide equilibrium without the need for continued introduction of fresh non reactor carbon monoxide to the reactor.

8. A process as claimed in claim 1, wherein the carbon dioxide feed is provided from recovery of carbon dioxide from a carbon dioxide source such as the atmosphere, the oceans and/or the effluent streams of industrial processes.

9. A process as claimed in claim 8, wherein the feed is provided via a two stage process comprising caustic scrubbing of carbon dioxide form the carbon dioxide source followed by electrolysis of the caustic/sodium carbonate mixture to release carbon dioxide.

10. A process as claimed in claim 1 wherein the hydrogenation reaction is undertaken at 400° C. or less.

11. A process as claimed in claim 1 wherein the hydrogenation reaction is undertaken at a pressure of 20 MPa (200 atm) or less.

12. A process as claimed in claim 1, wherein the hydrogen and carbon dioxide is introduced to the reactor in a 3:1 molar ratio.

13. A process as claimed in claim 1, wherein the hydrogenation catalyst comprises Cu and ZnO on alumina.

14. A process as claimed in claim 10 wherein the hydrogenation reaction temperature is between 150 and 300° C. 300° C.

15. A process as claimed in claim 11 wherein the hydrogenation reaction is undertaken at a pressure within the range of 5 to 20 MPa (50 to 200 atm).

16. A process as claimed in claim 10 wherein the hydrogenation reaction temperature is between 200 and 300°.

17. A process as claimed in claim 10 wherein the hydrogenation reaction temperature is between 210 to 270° C.

18. A process as claimed in claim 11 wherein the hydrogenation reaction is undertaken at a pressure within the range of 5 to 15 MPa (50 to 150 atm).

19. A process as claimed in claim 1 wherein the hydrogenation reaction is undertaken at 350° C. or less.

20. A process as claimed in claim 1 wherein the hydrogenation reaction is undertaken at 300° C. or less.

21. A process as claimed in claim 1 wherein the hydrogenation reaction is undertaken a pressure of 15 MPa (150 atm) or less.

22. A process as claimed in claim 1 wherein the hydrogenation reaction is undertaken a pressure of 10 MPa (100 atm) or less.

23. A process as claimed in claim 11 wherein the hydrogenation reaction is undertaken at a pressure of 5 MPa (50 atm).

* * * * *